US012478493B2

(12) United States Patent
Lin et al.

(10) Patent No.: US 12,478,493 B2
(45) Date of Patent: Nov. 25, 2025

(54) PATELLA BRACE HAVING CHIP

(71) Applicant: Ghi Fu Technology Co, Ltd., Changhua County (TW)

(72) Inventors: Li-Chi Lin, Changhua County (TW); Yi-Ying Lin, Changhua County (TW)

( * ) Notice: Subject to any disclaimer, the term of this patent is extended or adjusted under 35 U.S.C. 154(b) by 170 days.

(21) Appl. No.: 18/507,095

(22) Filed: Nov. 13, 2023

(65) Prior Publication Data

US 2025/0041093 A1 Feb. 6, 2025

(30) Foreign Application Priority Data

Jul. 31, 2023 (TW) ................................ 112128678

(51) Int. Cl.
*A61F 5/01* (2006.01)

(52) U.S. Cl.
CPC .... *A61F 5/0123* (2013.01); *A61F 2005/0172* (2013.01)

(58) Field of Classification Search
CPC .. A61F 5/30; A61F 13/061; A61F 2005/0176; A61F 13/107; A61F 5/24; A61F 5/32; A61F 5/34; A61F 5/0123; A61F 5/0106; A61F 2005/0172; A61F 2005/0174; A61F 2005/0181; A61H 7/001
See application file for complete search history.

(56) References Cited

U.S. PATENT DOCUMENTS

| | | | | | |
|---|---|---|---|---|---|
| 5,306,229 | A * | 4/1994 | Brandt | A61F 13/066 602/61 |
| 5,865,775 | A * | 2/1999 | Peoples | A61F 5/0118 602/62 |
| 6,077,242 | A * | 6/2000 | Falk | A61F 5/34 602/26 |
| 6,149,616 | A * | 11/2000 | Szlema | D04B 1/18 602/26 |
| 8,187,212 | B2 * | 5/2012 | Shmidman | A61F 5/34 602/61 |
| 2008/0300523 | A1 * | 12/2008 | Frishberg | A61F 5/0106 602/26 |
| 2015/0069640 | A1 * | 3/2015 | Lin | A61F 7/02 257/787 |
| 2015/0182409 | A1 * | 7/2015 | Julian | A61H 7/001 601/136 |
| 2016/0324674 | A1 * | 11/2016 | Scheuermann | A61F 5/30 |
| 2019/0046351 | A1 * | 2/2019 | Lin | A61F 7/086 |
| 2019/0364991 | A1 * | 12/2019 | Lee | A41D 13/088 |

* cited by examiner

*Primary Examiner* — Kari K Rodriquez
(74) *Attorney, Agent, or Firm* — Bruce Stone LLP; Joseph A. Bruce

(57) ABSTRACT

A patella brace having a chip is disclosed. The patella brace includes a strap, a pad and a chip. The strap has two ends each provided with a buckle. A hook-and-loop strap is insertedly connected to the buckles at the two ends of the strap. The pad is disposed in the strap. The pad has an upper surface, a lower surface, and at least one side surface. A support part is integrally formed with a middle portion of the upper surface. The side surface of the pad and a top surface and a side surface of the support part are concave surfaces. When in use, they are attached to and brace the patella for protecting the patella. A raised portion is provided on either end of the upper surface. A recess is formed on either end of the lower surface. The chip is disposed in the recess of the pad.

9 Claims, 8 Drawing Sheets

PATELLA BRACE HAVING CHIP

FIELD OF THE INVENTION

The present invention relates to a patella brace, and more particularly to a patella brace having a chip.

BACKGROUND OF THE INVENTION

A conventional patella brace includes a strap. Both ends of the strap are detachably bonded to each other. A shock-absorbing pad is provided in the middle of the strap. The shock-absorbing pad is closely attached to the surface of the knee to provide a good shock-absorbing and cushioning effect, so as to protect the knee and reduce injuries.

However, the conventional shock-absorbing pad of the patellar brace is in the form of a strip or a long plate. When the wearer moves or walks, the force of the impact will be concentrated on the shock-absorbing pad, which will cause deformation or stress concentration of the shock-absorbing pad. The wearer is prone to have the feeling of a foreign body. This makes the wearer feel uncomfortable, so the effectiveness of the product is reduced greatly. Accordingly, the inventor of the present invention has devoted himself based on his many years of practical experiences to solve these problems.

SUMMARY OF THE INVENTION

The primary object of the present invention is to provide a patella brace having a chip. When in use, the patella brace is attached to the patella for protecting the patella.

In order to achieve the foregoing object, the patella brace provided by the present invention comprises a strap, a pad and a chip. The strap has two ends each provided with a buckle. A hook-and-loop strap is insertedly connected to the buckles at the two ends of the strap. The pad is disposed in the strap. The pad has an upper surface, a lower surface, and at least one side surface. A support part is integrally formed with a middle portion of the upper surface. The support part has a top surface that is a concave surface and a side surface that is a concave surface. A raised portion is provided on either end of the upper surface. A recess is formed on either end of the lower surface. The recess corresponds in position to the raised portion. The side surface of the pad is a concave surface. The chip is disposed in the recess of the pad.

In the patella brace provided by the present invention, the side surface of the pad, the top surface and the side surface of the support part are concave surfaces. When in use, they are attached to and brace the patella for protecting the patella. Besides, the chip emits far-infrared rays, and the thermal reaction increases the subcutaneous temperature, thereby promoting the expansion of capillaries in the tendons or ligaments on both sides of the patella and accelerating blood circulation.

DETAILED DESCRIPTION OF THE PREFERRED EMBODIMENTS

Embodiments of the present invention will now be described, by way of example only, with reference to the accompanying drawings.

Figure 1:
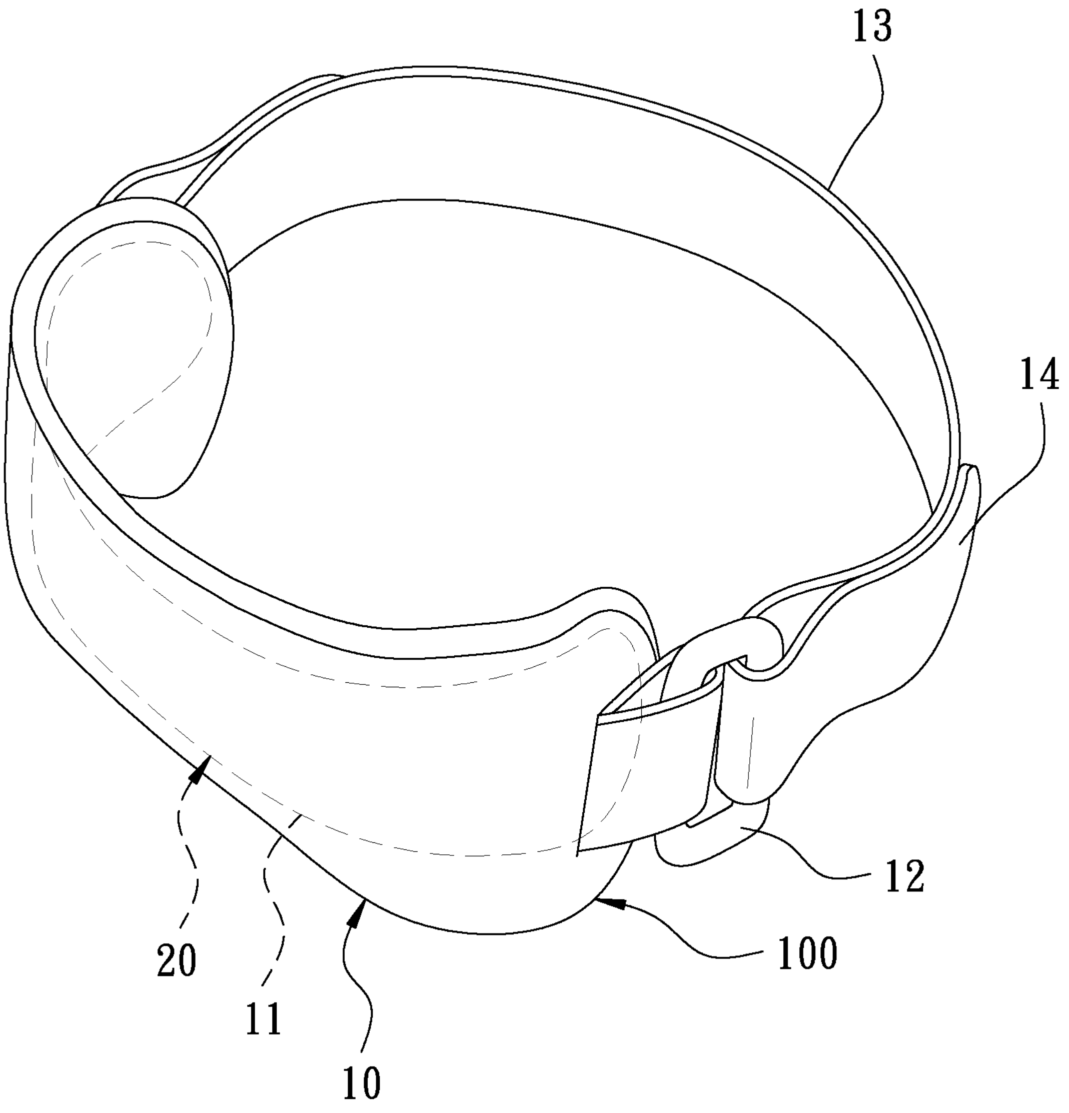
FIG. 1 is a perspective view in accordance with a first embodiment of the present invention.
Figure 2:
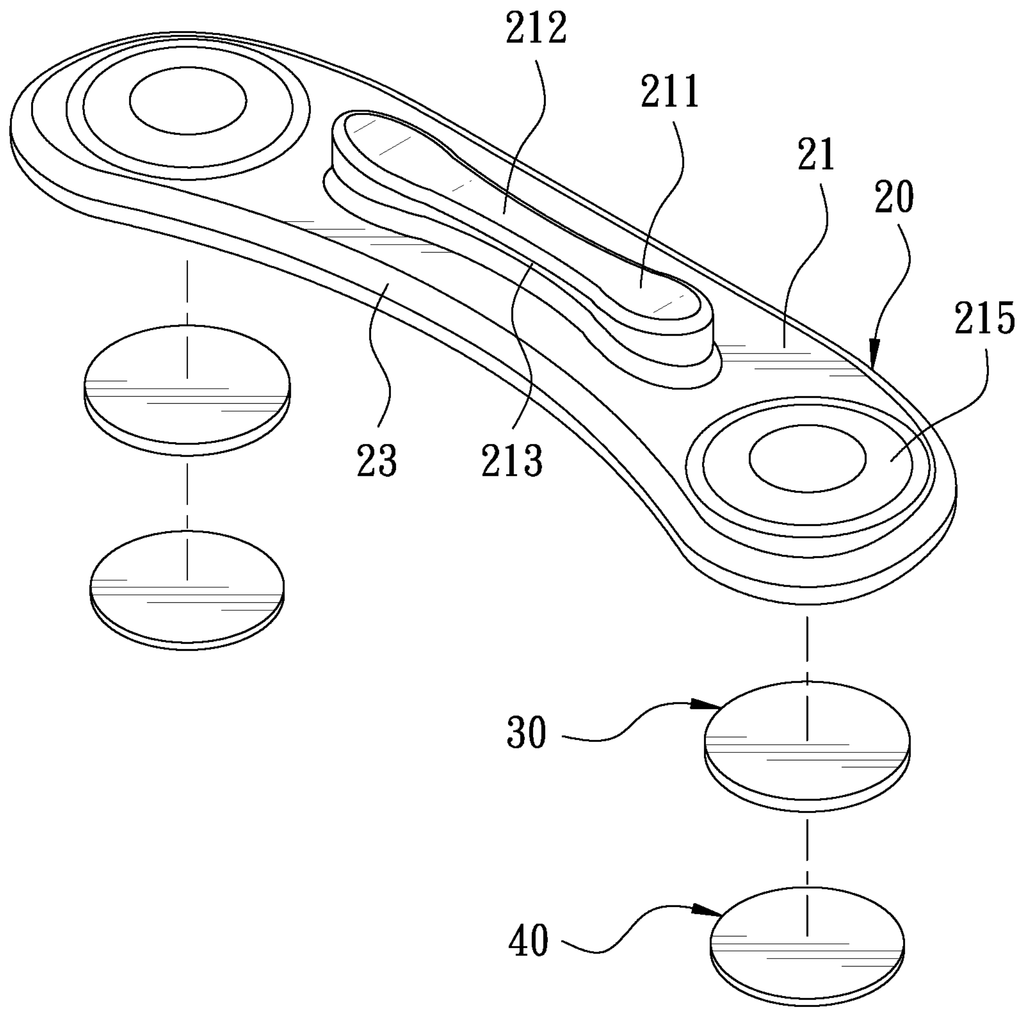
FIG. 2 is an exploded view in accordance with the first embodiment of the present invention.
Figure 3:
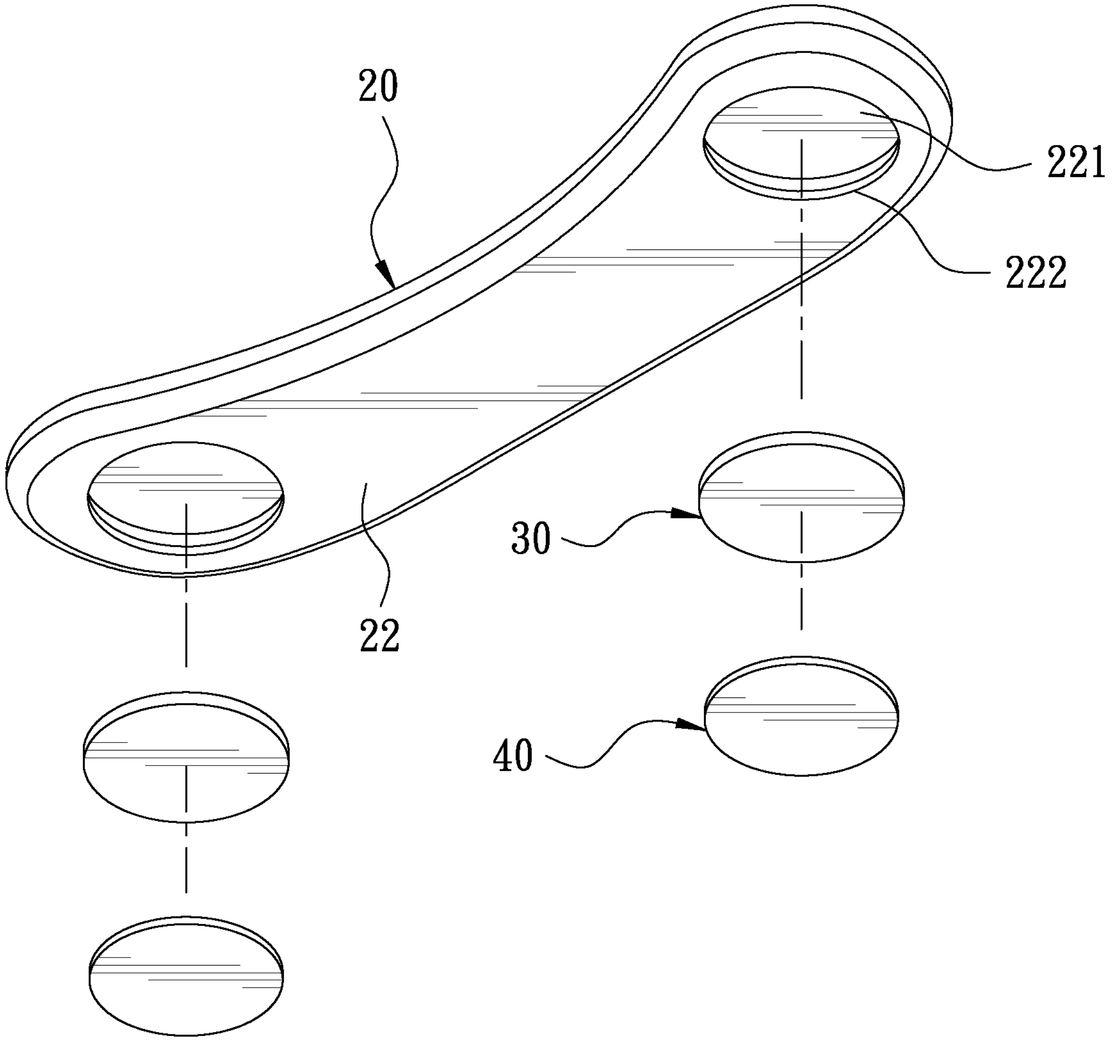
FIG. 3 is another exploded view in accordance with the first embodiment of the present invention.

FIG. 1 is a perspective view in accordance with a first embodiment of the present invention. FIG. 2 is an exploded view in accordance with the first embodiment of the present invention. FIG. 3 is another exploded view in accordance with the first embodiment of the present invention. The present invention discloses a patella brace 100 having a chip, comprising a strap 10, a pad 20, a chip 30, and a cover 40.

The strap 10 is an arc-shaped elongate strap. The strap 10 is composed of two fabrics sewn together, so that the strap 10 has an accommodation space 11 therein. Two ends of the strap 10 are each connected or sewn with a buckle 12. A hook-and-loop strap 13 is insertedly connected to the buckles 12 at the two ends of the strap 1. A hook-and-loop fastener 14 is provided at either end of the hook-and-loop strap 13 for wearing the patellar brace 100 on the human body.

Figure 4:
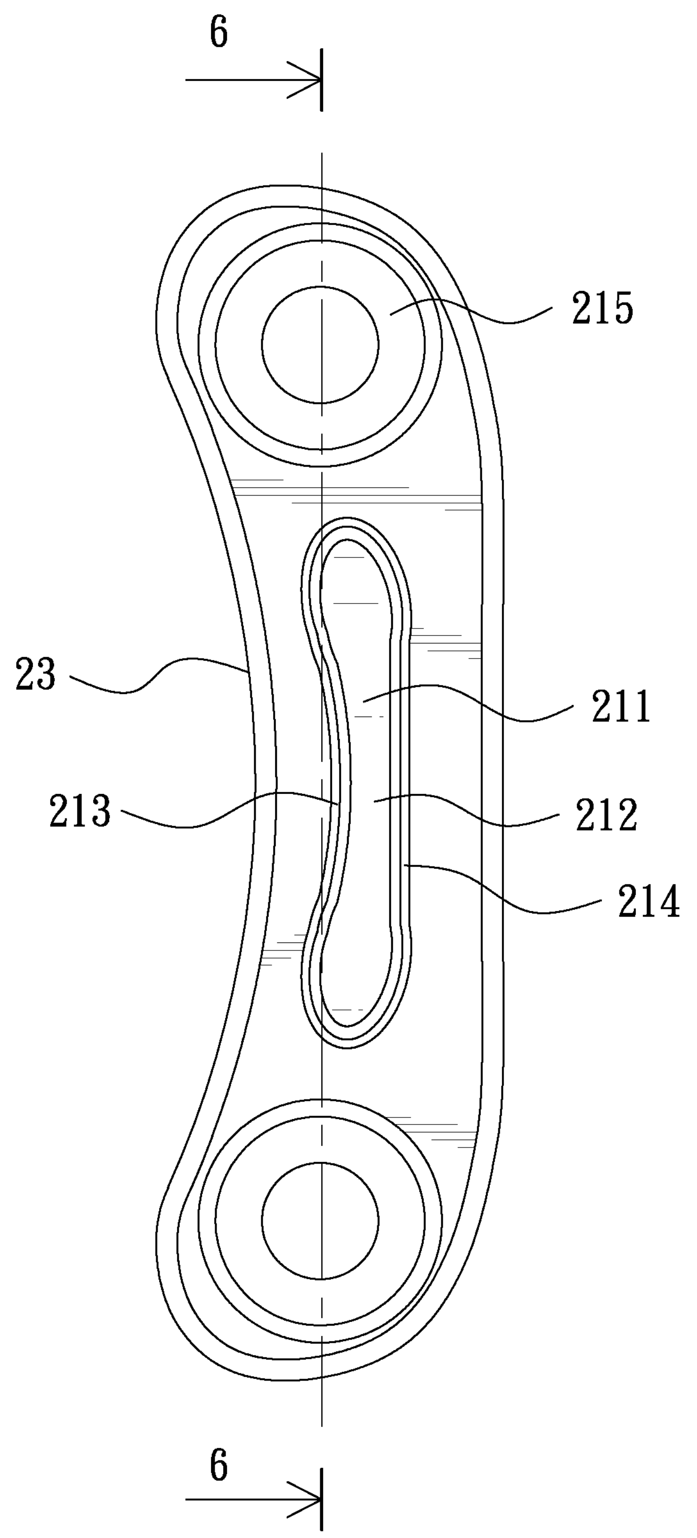
FIG. 4 is a top view of the pad in accordance with the first embodiment of the present invention.
Figure 5:
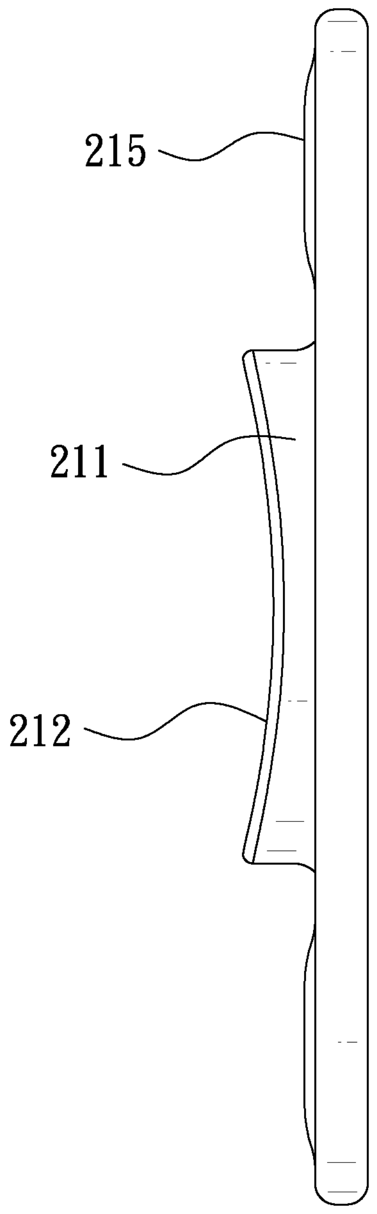
FIG. 5 is a side view of the pad in accordance with the first embodiment of the present invention.
Figure 6:
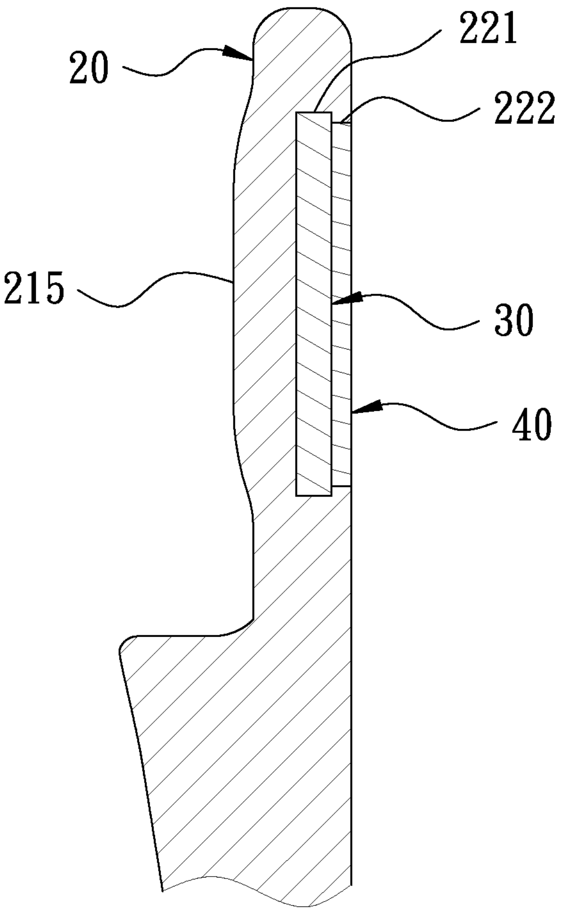
FIG. 6 is a cross-sectional view taken along line 6-6 of FIG. 4.

The pad 20, referring to FIG. 4 and FIG. 5, is disposed in the accommodation space 11 of the strap 10. In this embodiment of the present invention, the material of the pad 20 is silicone rubber. The hardness of the pad 20 is Shore A 20 to 40. The pad 20 has an upper surface 21, a lower surface 22, and at least one side surface 23. A support part 211 is integrally formed with a middle portion of the upper surface 21. The support part 211 is elongated, curved or rounded. The support part 211 has a top surface 212 that is a concave surface and a side surface 213 that is a concave surface. Another side surface 214 of the support part 211, away from the side surface 213, is a flat surface. A raised portion 215 is provided on either end of the upper surface 21. A recess 221 is formed on either end of the lower surface 22. As shown in FIG. 6, the shape of the recess 221 may be round, elliptical, or a shape without any pointed portions. In this embodiment, the recess 221 is a round recess. The bottom of the recess 221 corresponds in position to the raised portion 215. A flange 222 is provided at the opening of the recess 221. The side surface 23 of the pad 20 is a concave surface.

A transition surface, such as a rounded corner or a chamfer, may be disposed between the upper surface 21 and the side surfaces 23, 213, as well as between the top surface 212 and the side surface 213, so as to enhance wearing comfort.

The chip 30 is disposed in the recess 221 of the pad 20. The chip 30 includes a metal substrate. The metal substrate may be one of iron, zinc and aluminum and is thermally conductive. The surface of the metal substrate is sprayed with a coating. The coating contains a mixture of materials, such as germanium, carbon, calcium, silica, oxygen, and adhesive, mixed in proportion. The chip 30 will increase in temperature due to body heat and emit a far-infrared radiant energy. The shape of the chip 30 may be round, elliptical, or a shape without any pointed portions. In this embodiment, the shape of the chip 30 is round.

The cover 40 covers the chip 30 and is located within the flange 222 of the recess 221 of the pad 20. In this embodiment of the present invention, the material of the cover 40 is silicone rubber. The hardness of the cover 40 is Shore A 20 to 40. The shape of the cover 40 may be round, elliptical, or a shape without sharp corners. In this embodiment, the shape of the cover 40 is round.

Figure 7:
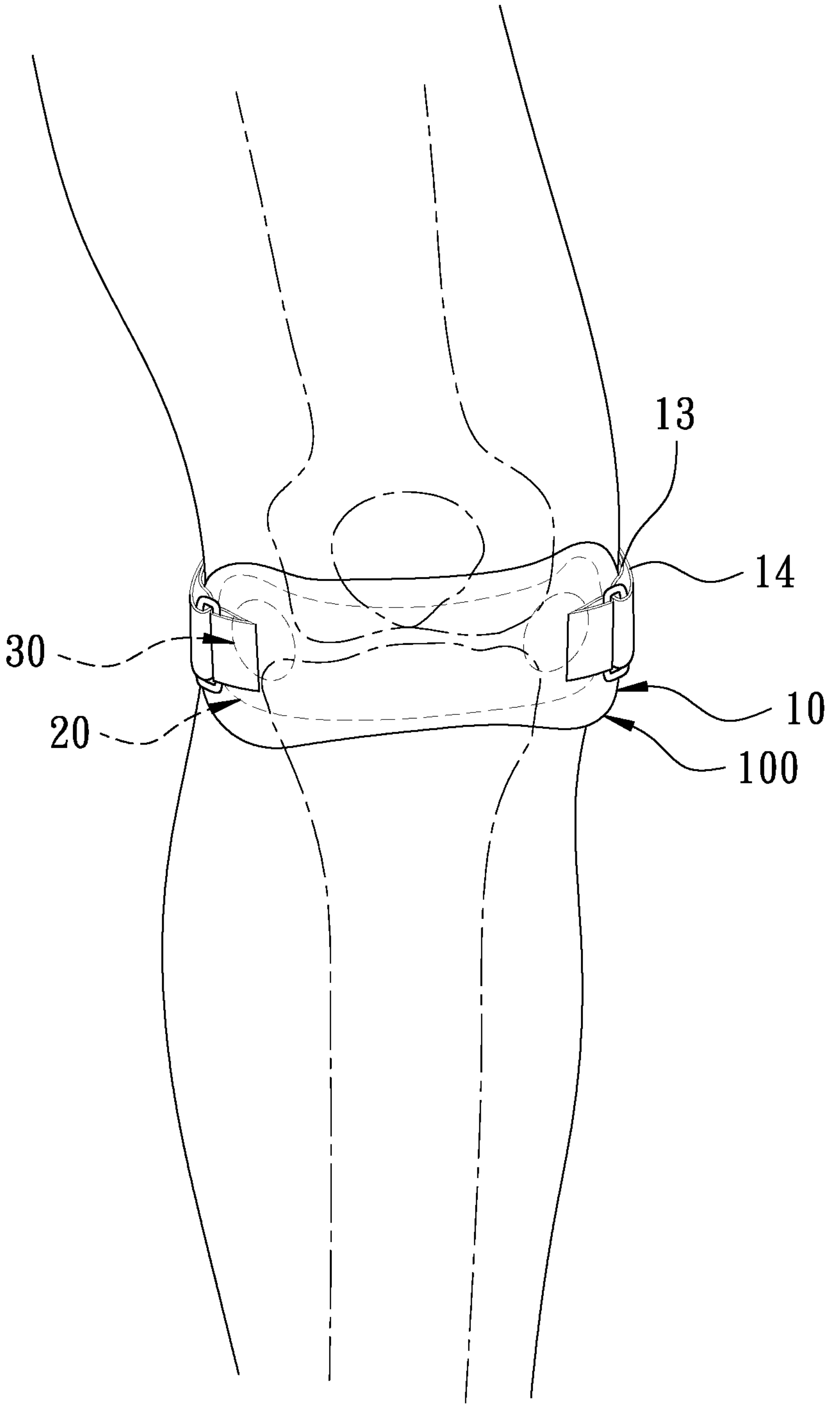
FIG. 7 is a schematic view showing the use of the first embodiment of the present invention.

Referring to FIG. 7, in cooperation with FIG. 2, FIG. 4 and FIG. 5, when in use, the direction of the patella brace 100 is first adjusted for the top surface 212 of the support part 211 to face the user, and the side surface 213 of the support part 211 to face upward, and the side surface 214 of the support part 211 to face downward. After that, the patella brace 100 is worn on the lower edge of the user's knee, and the side surface 23 of the pad 20, the top surface 212 and the side surface 213 of the support part 211 together brace the user's patella. Finally, the hook-and-loop strap 13 and the hook-and-loop fastener 14 are tightened to complete wearing the patellar brace 100. The side surface 23 of the pad 20, the top surface 212 and the side surface 213 of the support part 211 are concave surfaces that are attached to and brace the patella, in addition to stabilizing the patella, which can cushion the impact on the patella during the user's movement and disperse the impact force to the entire pad 20, so as to reduce the phenomenon of uneven distribution of force, increase the effect of force cushioning, and improve the support of the patellar brace 100, thereby achieving the effects of reducing sports injuries, alleviating pains, and protecting the patellar.

It is worth mentioning that the raised portion 215 of the pad 20 is used as a stimulation point to press against the tendons or ligaments on both sides of the patella. Besides, the raised portion 215 is configured to cushion the force and reduce the foreign body feeling of the chip 30 during wear. The chip 30 will increase in temperature due to body heat and emit far-infrared rays. The far-infrared rays can pass through the skin and resonate with water that accounts for 65%-70% of the body's water, causing the water to change from large molecules to small molecules and generating heat through inter-molecular friction. The thermal reaction increases the subcutaneous temperature, thereby promoting the expansion of capillaries in the tendons or ligaments on both sides of the patella, accelerating blood circulation, promoting metabolism, and removing harmful substances and heavy metals from the body. The new enzyme rapidly produces living cells, so that the body's physiological functions are more active, increasing immunity and keeping the user healthy and away from diseases.

Figure 8:
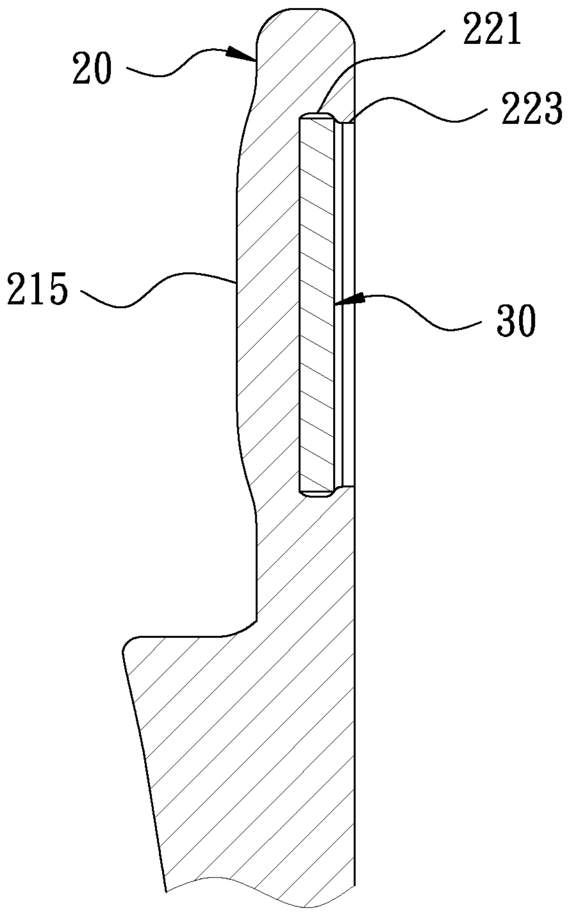
FIG. 8 is a cross-sectional view in accordance with a second embodiment of the present invention, illustrating the neck.

FIG. 8 illustrates a second embodiment. The difference between the second embodiment and the first embodiment of the present invention is that a neck 223 is provided at the opening of the recess 221 of the pad 20. The diameter of the neck 223 is less than the diameter of the recess 221. The recess 221 is only equipped with the chip 30, without the cover 40. When in use, the chip 30 is installed by slightly stretching the recess 221. The chip 30 is prevented from detaching from the recess 221 through the neck 223 of the recess 221, thereby achieving the effect of quick assembly.

What is claimed is:

1. A patella brace, comprising:

a strap, having two ends each provided with a buckle, a hook-and-loop strap being insertedly connected to the buckles at the two ends of the strap;

a pad, disposed in the strap, the pad having an upper surface, a lower surface, two opposite ends, and at least one side surface, a support part being integrally formed with and extending upwardly from a middle portion of the upper surface, the support part having a top surface that is a concave surface and a side surface that is a concave surface, a raised portion being provided at each of the two opposite ends of the upper surface, a recess being formed on each end of the lower surface, the recess corresponding in position to the raised portion, the side surface of the pad being a concave surface;

a chip, disposed in the recess of the pad;

wherein the chip includes a metal substrate, the metal substrate is one of iron, zinc and aluminum and is thermally conductive, a surface of the metal substrate is sprayed with a coating, and the coating contains a mixture of germanium, carbon, calcium, silica, oxygen and adhesive that are mixed in proportion.

2. The patella brace as claimed in claim 1, wherein the strap is an arc-shaped elongate strap, the strap is composed of two fabrics sewn together, the strap has an accommodation space therein, and the pad is disposed in the accommodation space of the strap.

3. The patella brace as claimed in claim 1, wherein a flange is provided at an opening of the recess, a cover is provided within the flange, the cover covers the chip, the cover is made of silicone rubber, and the cover has a hardness of Shore A 20 to 40.

4. The patella brace as claimed in claim 1, wherein a neck is provided at an opening of the recess of the pad.

5. The patella brace as claimed in claim 1, wherein the pad is made of silicone rubber, and the pad has a hardness of Shore A 20 to 40.

6. The patella brace as claimed in claim 1, wherein a hook-and-loop fastener is provided at either end of the hook-and-loop strap.

7. The patella brace as claimed in claim 1, wherein the support part has another side surface that is a flat surface.

8. The patella brace as claimed in claim 1, wherein the support part is elongated, curved or rounded.

9. The patella brace as claimed in claim 1, wherein the recess is a round recess, and the chip has a round shape.

* * * * *